United States Patent
Curcio et al.

(10) Patent No.: US 9,423,394 B2
(45) Date of Patent: Aug. 23, 2016

(54) RETINAL PIGMENT EPITHELIAL PRIMARY CELL CULTURE SYSTEM PRODUCING SUBCELLULAR DEPOSITS

(71) Applicant: TheraOptix, Inc., San Jose, CA (US)

(72) Inventors: Christine A. Curcio, Birmingham, AL (US); Clyde Guidry, Birmingham, AL (US)

(*) Notice: Subject to any disclaimer, the term of this patent is extended or adjusted under 35 U.S.C. 154(b) by 68 days.

(21) Appl. No.: 14/106,137

(22) Filed: Dec. 13, 2013

(65) Prior Publication Data

US 2015/0168378 A1    Jun. 18, 2015

(51) Int. Cl.
  *C12Q 1/00* (2006.01)
  *C12N 5/00* (2006.01)
  *G01N 33/50* (2006.01)
  *C12N 5/079* (2010.01)

(52) U.S. Cl.
  CPC ......... *G01N 33/5058* (2013.01); *C12N 5/0621* (2013.01); *G01N 33/5035* (2013.01)

(58) Field of Classification Search
  CPC .................................................. C12N 5/0621
  See application file for complete search history.

(56) References Cited

PUBLICATIONS

Amin et al., Modulation of sub-RPE deposits in vitro: a potential model for age-related macular degeneration. Investigative Ophthalmology & Visual Science, vol. 45, No. 5 (May 2004) pp. 1281-1288.*
Dunn et al., ARPE-19, a human retinal pigment epithelial cell line with differentiated properties. Experimental Eye Research, vol. 62 (1996) pp. 155-169.*
Corning Surface Areas and Recommended Medium Volumes for Corning® Cell Culture Vessels. Datasheet [online]. Corning, Inc., Sep. 2008 [retrieved on Jun. 27, 2015]. Retrieved from the Internet: <URL:http://csmedia2.corning.com/LifeSciences/Media/pdf/cc_surface_areas.pdf>.*
Maminishkis et al., Confluent monolayers of cultured human fetal retinal pigment epithelium exhibit morphology and physiology of native tissue. Retinal Cell Biology, vol. 47 No. (Aug. 2006) pp. 3612-3624.*
Curcio et al. "Aging, age-related macular degeneration, and the response to retention of apolipoprotein B-containing lipoproteins." *Prog. Ret. Eye Res.* 28:393-422 (2009).
Grisanti et al. "Transdifferentiation of retinal pigment epithelial cells from epithelial to mesenchymal phenotype." *Invest. Opthamol. Vis. Sci* 36(2):391-405 (1995).
Guidry et al. "Phenotypic variation of retinal pigment epithelium in age-related macular degeneration." *Invest. Opthamol. Vis. Sci* 43(1):267-273 (2002).
Johnson et al. "Cell culture model that mimics drusen formation and triggers complement activiation associated with age-related macular degeneration," *Proc. Natl. Acad. Sci, USA* 108:18277-18282 (2011).
Li et al. "Retina expresses microsomal triglyceride transfer protein: implications for age-related maculopathy." *J Lipid Res.* 46:628-640 (2005).
Mamballikalathil et al. "Tractional force generation by porcine Muller cells: paracrine stimulation by retinal pigment epithelium," *Invest. Opthamol. Vis. Sci* 41(2):529-536 (2000).
Mukherjee et al. "Phenotype-associated changes in retinal pigment epithelial cell expression on insulin-like growth factor binding proteins." *Invest. Opthamol. Vis. Sci* 50(11):5449-5455 (2009).
International Search Report (2 pages) for PCT/US2014/069594 dated Mar. 25, 2015.
Written Opinion (11 pages) of International Search Authority for PCT/US2014/069594 dated Mar. 25, 2015.

* cited by examiner

*Primary Examiner* — Kara Johnson

(57) ABSTRACT

The present invention provides a retinal pigment epithelial (RPE) primary cell culture system on a material surface seeded at a high density that produces a layer of subcellular deposits, wherein the RPE primary cells are harvested from non-fetal tissue. The present invention additionally provides methods of making and using the PRE primary cell culture system.

20 Claims, 3 Drawing Sheets

RETINAL PIGMENT EPITHELIAL PRIMARY CELL CULTURE SYSTEM PRODUCING SUBCELLULAR DEPOSITS

STATEMENT OF GOVERNMENT SUPPORT

This invention was made with government support under Grant No R01 EY06109 awarded by The National Institutes of Health/National Eye Institute. The government has certain rights in the invention.

FIELD OF THE INVENTION

The present invention provides a retinal pigment epithelial primary cell culture system and methods of making and using the cell system.

BACKGROUND OF THE INVENTION

Age-related macular degenerations (AMD) is a highly prevalent retinal disease in the elderly. The most prominent histopathological and clinical signs of AMD are subcellular lesions (drusen and basal linear deposits), which are neutral lipid-rich subcellular lesions that develop behind the retinal pigment epithelium. Drusen and BLinD are two physical forms—lump and layer—of the same lipid-rich lipoprotein derived debris. Progress towards understanding pathogenic mechanisms involved in macular degeneration and testing new treatments has been hindered by the lack of an accurate model system such as an engineered mouse that exhibits the pathognomonic lesions of the disease, (e.g., drusen and basal linear deposits (BlinD).

The RPE is simple cuboidal epithelium specialized to maintain the health of photoreceptors and the choroidal vasculature while maintaining the outer limits of the physiological blood-retina barrier. Research shows that RPE cells are phenotypically unstable when removed from their host eye and maintained under routine tissue culture conditions. Under these conditions, RPE can undergo a progression of phenotype changes resulting in cells that resemble myofibroblasts rather than epithelia. (Guidry et al. *Invest. Ophthalmol. Vis. Sci.* 43(1):267-273 (2002)). For this reason, the overwhelming majority of research published in the scientific literature involves immortalized cell lines, fetal cells or primary cells that have trans-differentiated into the myofibroblast phenotype.

The present invention overcomes previous shortcomings in the art by providing a RPE primary cell system that produces subcellular deposits as model for the study of macular degeneration.

SUMMARY OF THE INVENTION

In a first aspect, the present invention provides a retinal pigment epithelial (RPE) primary cell culture system on a material surface seeded at a high density that produces a layer of subcellular deposits, wherein the RPE primary cells are harvested from non-fetal tissue.

In a second aspect, the present invention provides a method of producing a retinal pigment epithelial (RPE) primary cell culture system that produces a layer of subcellular deposits, comprising: (a) seeding RPE primary cells on a material support at a high density, wherein said RPE primary cells are harvested from non-fetal tissue; and (b) culturing the RPE primary cells seeded on said material surface without subculturing, thereby producing a RPE primary cell culture system that produces a layer of subcellular deposits.

In a third aspect, the present invention provides a method of maintaining an epithelial phenotype in a retinal pigment epithelial (RPE) primary cell, comprising (a) seeding RPE primary cells at a high density on a material support, wherein said RPE primary cells are harvested from non-fetal tissue; and (b) culturing the RPE primary cells on said material surface without subculturing, thereby maintaining the epithelial phenotype in said RPE cells.

In a fourth aspect, method of producing a layer of subcellular deposits from a retinal pigment epithelial (RPE) primary cell culture system, comprising: (a) seeding RPE primary cells at a high density on a material support, wherein said RPE primary cells are harvested from non-fetal tissue; and (b) culturing the RPE primary cells seeded on said material surface without subculturing, thereby producing an RPE primary cell culture system that produces a layer of subcellular deposits.

In a fifth aspect, a method of identifying a test agent that modulates the amount of subcellular deposits produced in an RPE primary cell culture system, comprising: contacting the RPE primary cell culture system of this invention with the test agent; and determining the amount of subcellular deposits produced by the RPE primary cell culture system contacted with said test agent as compared to a control RPE primary cell culture system not contacted with said test agent, thereby identifying a test agent that modulates the amount of subcellular deposits produced by the RPE primary cell culture system.

In a sixth aspect, the present invention provides a method for identifying an agent for treating macular degeneration, comprising: contacting the RPE primary cell culture system of this invention with the agent; and determining the amount of subcellular deposits produced by the RPE primary cell culture system contacted with said agent as compared to a control RPE primary cell culture system not contacted with said agent, wherein an agent that reduces the amount of, prevents the accumulation of, or prevents further accumulation of subcellular deposits produced by said RPE primary cell culture system contacted with said agent as compared to a control RPE primary cell culture system not contacted by said agent is identified as an agent for treating macular degeneration.

These and other aspects of the invention will be set forth in more detail in the description of the invention that follows.

BRIEF DESCRIPTION OF THE FIGURES

FIG. 3 (bottom) shows primary porcine RPE on a Transwell filter, stained with oil red and counterstained with hematoxylin for nucleic acid in cellular nuclei and calcium within the sub- RPE deposits. This figure shows oil red O binding lipid between the RPE and the support, as well as in the pores that cross the support (vertical lines).

DETAILED DESCRIPTION OF THE INVENTION

Figure 1:
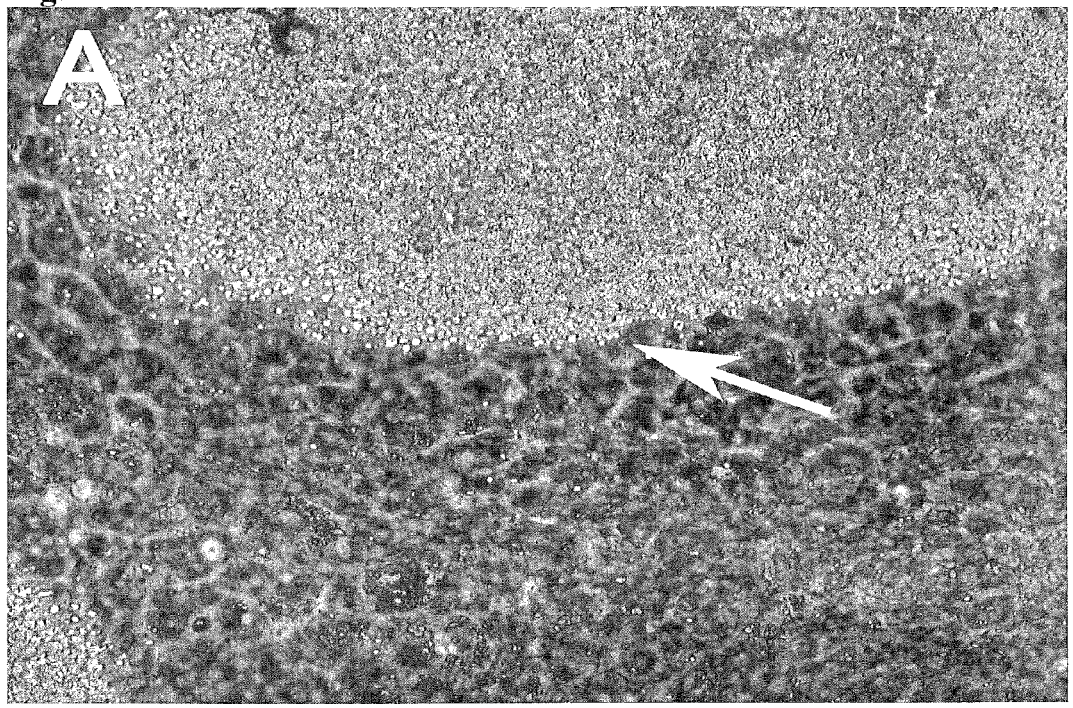
FIG. 1A-1B show RPE drusen by phase contrast (A) and dark field (B) microscopy. The interface between areas with and without drusen is indicated by the arrow. Dark field microscopy indicates the crystalline nature of the deposits.
Figure 1:
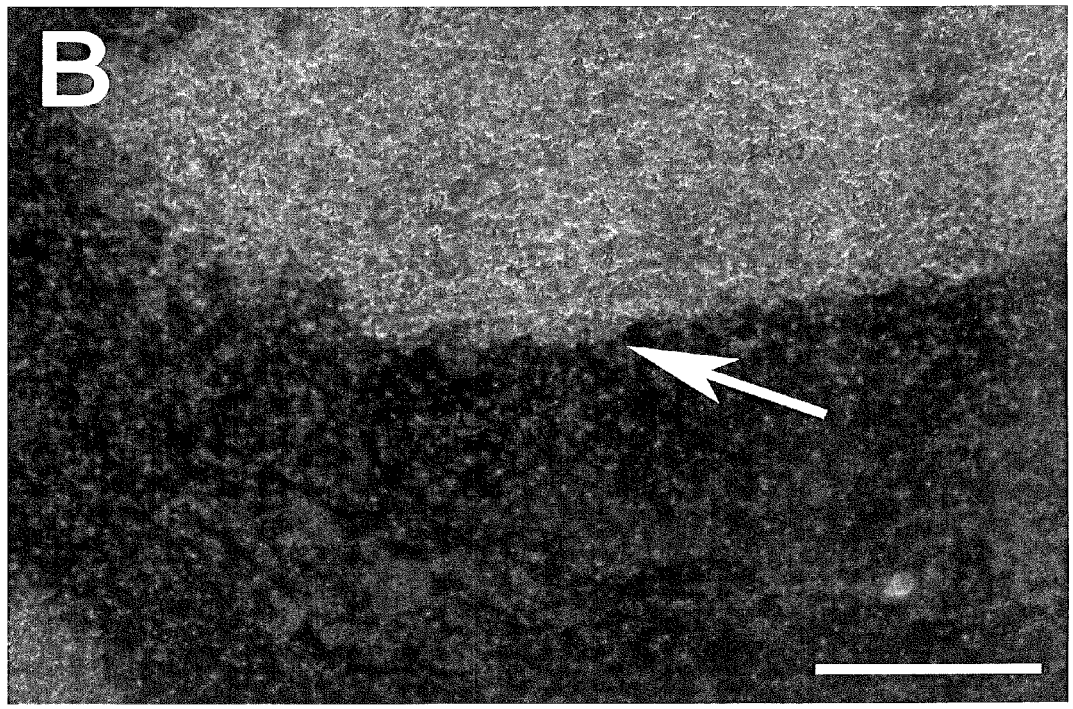
Figure 2:
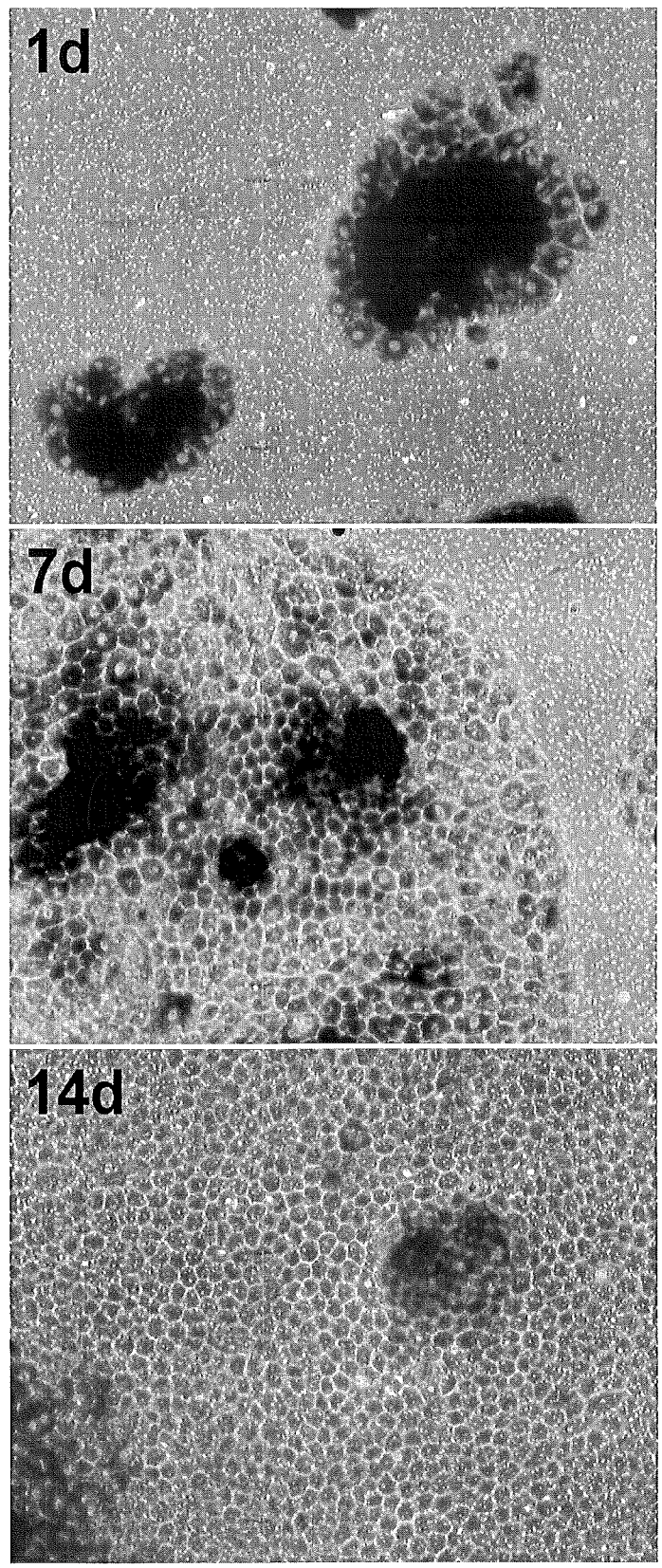
FIG. 2 shows a phase contrast image of RPE cultures on transwell membrane from the initial isolation to 14 days (1 day, 7 days and 14 days).

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, patent publications, and other references cited herein are incorporated by reference in their entireties for the teachings relevant to the sentence and/or paragraph in which the reference is presented.

As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, refers to variations of ±20%, ±10%, ±5%, ±1%, ±0.5%, or even ±0.1% of the specified amount.

The terms "modulate," "modulates," "modulated" or "modulation" refer to enhancement (e.g., an increase) or inhibition (e.g., a reduction) in the specified activity (e.g., production of subcellular deposits). A modulator is an agent (e.g., a chemical agent, or a biological agent, and the like) which modulates an activity (e.g., production of subcellular deposits or a layer of subcellular deposits).

The term "agent," "test agent," "test compound" or "candidate agent" refers to any chemical agent, biological agent, pharmaceutical, drug, and the like, that can be used to treat and/or prevent a disease, illness, sickness, or disorder of bodily function, and/or otherwise alter the physiological and/or cellular status of a sample (e.g., the amount of subcellular deposits produced by the RPE primary cell system of this invention). Test compounds comprise both known and potential therapeutic compounds. A test compound can be determined to be therapeutic by using the screening methods of the present invention.

As used herein "biological agent" refers to a substance that is made from a living organism or its products and is used in the prevention, diagnosis, and/or treatment of a disease. Biological agents include antibodies, antibiotics, anti-virals, interleukins, agents that alter protein phosphorylation and/or protein activity, block or inhibit receptor function, alter DNA methylation, effect DNA repair, alter protein expression, alter RNA expression, alter RNA splicing, vaccines and/or the like.

By the terms "treat," "treating," or "treatment of" (and grammatical variations thereof) it is meant that the severity of the subject's condition is reduced, at least partially improved, or stabilized and/or that some alleviation, mitigation, decrease, or stabilization in at least one clinical symptom and/or parameter is achieved and/or there is a delay in the progression of the disease or disorder.

The terms "prevent," "preventing," and "prevention" (and grammatical variations thereof) refer to avoidance, prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

The terms "prevent," "preventing," and "prevention" (and grammatical variations thereof) refer to prevention and/or delay of the onset of an infection, disease, condition and/or a clinical symptom(s) in a subject and/or a reduction in the severity of the onset of the infection, disease, condition and/or clinical symptom(s) relative to what would occur in the absence of the methods of the invention. The prevention can be complete, e.g., the total absence of the infection, disease, condition and/or clinical symptom(s). The prevention can also be partial, such that the occurrence of the infection, disease, condition and/or clinical symptom(s) in the subject and/or the severity of onset is less than what would occur in the absence of the present invention. Thus, the terms "prevent," "preventing," and "prevention" and like terms are used herein to include imparting any level of prevention or protection which is of some benefit to a subject, such that there is a reduction in the incidence and/or the severity of the disease in a treated subject, regardless of whether the protection or reduction in incidence and/or severity is partial or complete. With respect to an infection, a disease, and/or a condition in a subject, the term refers to, e.g., preventing the infection, disease, and/or condition from occurring if the treatment is administered prior to the onset of the infection, disease, or condition.

As used herein, the terms "reduce," "reduced," "reducing," "reduction," "diminish," "suppress," and "decrease" (and grammatical variations thereof), describe, for example, a decrease in production of subcellular deposits as compared to a control as described herein. Thus, as used herein, the terms "reduce," "reduces," "reduced," "reduction," "diminish," "suppress," and "decrease" and similar terms mean a decrease of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%, or any range therein, as compared to a control (e.g., a RPE primary cell culture system not contacted with an agent).

As used herein, "subcellular deposit" means a deposit secreted from and located outside the RPE cell. These deposits are produced and secreted below the RPE cells (e.g., sub-RPE) when grown on a material structure. Thus, the deposits produced by the RPE cells are secreted out of the cells and deposited between the RPE cells and the material surface. These subcellular deposits can accumulate and coalesce to form a confluent layer below the cell layer that can eventually become confluent with the culture vessel in which the cell culture system is growing. Notably, the layers of subcellular deposits produced by the RPE cells of the RPE primary cell culture system that form below the RPE cells can elevate the cells of the cell culture system and disturb the adhesion of the cells to the material surface, thereby undermining the cells similar to the disease state of AMD. The deposits that are produced are greater than 0.4 µm in size as they are not found in the pores of Transwell culture vessels (the pores of which are 0.4 µm in size). Thus, in representative embodiments, the deposits produced by the RPE cells of the RPE primary cell culture system of this invention are greater than 0.4 µm in size (e.g., greater than 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm, and the like, and any value or range therein.

In some embodiments, the subcellular deposits produced by the PRE primary cell culture system are neutral lipid-rich deposits, for example, drusen and basal linear deposits (BlinD). The deposits described herein are those located in the sub-RPE compartment, on the inner surface of Bruch's membrane, where conventional drusen are located. In representative embodiments, the subcellular deposits produced by the RPE primary cell culture system of this invention are drusen and/or basal linear deposits (BlinD). In some aspects, the RPE cells of the RPE primary cell culture system have zonula occludens (tight junctions).

As used herein, a "cell culture system" is a culture of cells grown and maintained on a material surface.

The RPE cells of the present invention are "primary cells." As well known in the art, primary cells are obtained directly from the tissues of an organism and established for in vitro growth (e.g., seeded onto a material surface). Such cells have not been "passaged" and have undergone very few population doublings. As a result, these types of cells are considered to be more representative of the tissue from which they are derived and thus more representative of the in vivo state than, for example, immortalized continuous cell lines. Notably, primary cells are generally anchorage dependent, adherent cells and therefore, grow in vitro when seeded onto a material surface.

Most cell biologists work with non-primary cells, which are transformed cell lines (e.g., immortalized cells) because these cells are relatively easy to work with and their phenotype is stable. There are about four to five immortalized RPE cell lines available but they are not phenotypically similar to native RPE in that rather than resembling epithelia they resemble myofibroblasts. Johnson et al. describe a human fetal RPE cell line (*Proc. Natl. Acad. Sci.* 108(45): 18277-18282 (2011)), which resemble native RPE more closely than non-primary RPE cell lines, but produce particulate "deposits" that do not aggregate and do not form layers beneath the cells. Therefore, the particulate "deposits" produced by these human fetal cell lines are less characteristic of macular degeneration and are a less accurate cell model for the macular degeneration phenotype than the RPE cell culture system of the present invention, which coalesce to form continuous sub-cellular layers. It is noted that the particulates produced by the cell line of Johnson et al. are secreted into the wells/pores of the transwells culture vessels, which are about 0.4 µm in size. Thus, the particulates produced by the cell line of Johnson et al. are 0.4 µm or smaller. The deposits produced by the RPE cells of RPE primary cell culture system of this invention are not secreted into transwell pores but instead accumulate and coalesce below the RPE cells to form a subcellular layer. This subcellular layer of deposits produced by the RPE cells of RPE primary cell culture system of this invention actually elevate the cells of the cell culture system and disturb the adhesion of the cells to the material surface, thereby undermining the cells much the same as occurs in age related macular degeneration disease state. Thus, while apparently producing the molecular components of drusen (e.g., apolipoprotein E), the cell lines of Johnson et al. do not replicate the physical characteristics of drusen and basal linear deposit typical of AMD. That is, the human fetal cell lines of Johnson et al. do not produce deposits that coalesce to form a continuous subcellular layer that could block transport between the choriocapillaris blood supply and outer retinal cells as is observed in AMD. Finally, the very few researchers that do work directly with primary RPE cells seed them in the cell culture at a low density, which results in the cells changing phenotype from epithelial cells to myofibroblasts.

As used herein, a "material surface" can be any structure upon which a cell can grow and proliferate as an adherent culture (e.g., the cells can bind and adhere to said structure). As used herein, "material surface" means any deformable or non-deformable surface (versus a liquid) that the RPE primary cells can adhere to including but not limited to plastic, glass, collagen gel, laminin gel, enactin gel, and the like, or any combination thereof. In some embodiments, the material surface can be coated with an extracellular matrix (e.g., collagen and/or laminin, and the like) to increase adhesion properties and provide other signals needed for growth and differentiation of the cells. Nonlimiting examples of a structure for said material surface (e.g., culture vessel) can include cylindrical, test tube-like, tube-like, tube, rod-like, rod, flat, sheet-like, sheet, test strip, strip-like, strip, bead, microbead, well, plate, tissue culture plate, petri plate, microplate, microtiter plate, flask, stick, vial, spherical, bead-like, bead, and paddle. Further, non-limiting examples of a material surface can include tissue culture plastic, glass, polystyrene, polypropylene, polyethylene, dextran, nylon, amylases, natural and modified celluloses, polyacrylamides, gabbros, magnetite, soluble material, magnetic material, and nonmagnetic material. A solid support may be magnetic or non-magnetic. Those skilled in the art will be aware of or be readily able to identify many other suitable carriers for binding cells. Adherent culture can also involve growing cells in a three-dimensional (3-D) environment as opposed to two-dimensional culture vessels.

Thus, the present invention is directed to the provision of a model system for the study of macular degeneration and the production of subcellular lesions by RPE. This is the first model RPE cell system that produces drusen and BlinD characteristic of the pathognomonic lesions produced in the macular degeneration disease state. As such, the RPE primary cell culture system of this invention will be useful for studying, for example, the biology of lipoprotein pathways in polarized RPE and for testing various routes of lesion abrogation.

Accordingly, a first aspect of the invention provides a retinal pigment epithelial (RPE) primary cell culture system on a material surface initially seeded at a high density that produces a layer of subcellular deposits, wherein the RPE primary cells are harvested from non-fetal tissue. In some aspects of the invention, the cells in the RPE primary cell culture system seeded at a high density on the material surface are contact inhibited and phenotype arrested. In other aspects, the cells in the RPE primary cell culture system are in a confluent monolayer on the material surface. In still other aspects, the cells are not in a confluent monolayer on the material surface.

In other embodiments, methods for making the RPE primary cell culture system of this invention are provided.

Accordingly, in one aspect, a method of producing a retinal pigment epithelial (RPE) primary cell culture system that produces a layer of subcellular deposits, comprising: (a) seeding RPE primary cells on a material support at a high density, wherein said RPE primary cells are harvested from non-fetal tissue; and (b) culturing the RPE primary cells seeded on said material surface without subculturing, thereby producing a RPE primary cell culture system that produces a layer of subcellular deposits.

In some aspects, the present invention provides a method of maintaining an epithelial phenotype in a retinal pigment epithelial (RPE) primary cell, comprising (a) seeding RPE primary cells at a high density on a material support, wherein said RPE primary cells are harvested from non-fetal tissue; and (b) culturing the RPE primary cells on said material surface without subculturing, thereby maintaining the epithelial phenotype in said RPE cells.

In other aspects, a method of producing a layer of subcellular deposits from a retinal pigment epithelial (RPE) primary cell culture system, comprising: (a) seeding RPE primary cells at a high density on a material support, wherein said RPE primary cells are harvested from non-fetal tissue; and (b) culturing the RPE primary cells seeded on said material surface without subculturing, thereby producing an RPE primary cell culture system that produces a layer of subcellular deposits.

Any method for harvesting cells for purpose of in vitro cell growth onto a material surface can be used with the present invention and such methods are well known in the art.

In further aspects of the invention, the RPE cells of the RPE primary cell culture system of this invention are harvested from non-fetal tissue from any appropriate organism including, but not limited to, a mammal, a bird, a reptile, an amphibian, and/or a fish. Mammalian organisms can include, but are not limited to, humans, non-human primates (e.g., monkeys, chimpanzees, baboons, etc.), dogs, cats, mice, hamsters, rats, horses, cows, pigs (porcine), rabbits, sheep and goats. Avian organisms can include, but are not limited to, chickens, turkeys, ducks, geese, quail and pheasant, and birds kept as pets (e.g., parakeets, parrots, macaws, cockatoos, and the like).

Any method appropriate for the harvesting of cells from the eye of an organism can be used with this invention. See, for example, Mamballikalathil et al. (2000 *Invest. Opthalmol. Vis. Sci.* 41:529-536) and Grisanti and Guidry (1995 *Invest. Opthalmol. Vis. Sci.* 36:391-405).

An exemplary method of establishing primary cultures of RPE cells from freshly enucleated eyes includes transporting dissected globes to the laboratory in ice-cold normal saline. In representative embodiments, the RPE primary cells are from the eye of an organism excised from said organism 0 to 60 min post-mortem. Thus, in some embodiments, the eye from which the RPE cells are harvested is excised from the organism 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes post mortem.

In some embodiments, the cells can be released from posterior eyecups enzymatically (e.g., by treatment with trypsin, at a concentration of, for example, 0.25%, and ethylenediaminetetraacetic acid (EDTA), at a concentration of, for example, 0.02% (Gibco, Grand Island, N.Y.)). In general, the cells are released from the eye and placed onto a material support (e.g., a culture vessel) in about 1 minute to about 24 hours postmortem, about 1 minute to about 12 hours postmortem, about 1 minute to about 4 hours post mortem, about 1 hour to about 24 hours postmortem, about 1 hour to about 12 hours postmortem or about 4 hours to about 12 hours postmortem. Thus, in some embodiments, the cells are released from the eye and placed onto a material support (e.g., culture vessel) in about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 325, 350, 375, 400, 425, 450, 475, 500, 525, 550, 575 600, 625, 650, 675, 700, 725, 750, 775, 800, 825, 850, 875, 900, 925, 950, 975, 1000, 1050, 1100, 1150, 1200, 1250, 1300, 1350, 1400, 1450 minutes postmortem, or any amount or range therein; or 1, 1.25, 1.5, 1.75, 2, 2.25, 2.5, 2.75, 3, 3.25, 3.5, 3.75, 4, 4.25, 4.5, 4.75, 5, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 14.75, 15, 15.25, 15.5, 15.75, 16, 16.25, 16.5, 16.75, 17, 17.25, 17.5, 17.75, 18, 18.25, 18.5, 18.75, 19, 19.25, 19.5, 19.75, 20, 20.25, 20.5, 20.75, 21, 21.25, 21.5, 21.75, 22, 22.25, 22.5, 22.75, 23, 23.25, 23.5, 23.75, 24, hours postmortem, or any amount or range therein.

In some embodiments, the RPE primary cells can be purified using density gradient centrifugation prior to seeding onto the material surface. A high density cushion can comprise polyacrylamide (e.g., PERCOL®), hydrophilic polysaccharide (e.g., FICOL®), sucrose, or any other appropriate material for separating cells. The skilled cell biologist would be aware of what materials are appropriate for cell separation using high density centrifugation. In some embodiments, the cushions comprise about 1% to about 50% polyacrylamide (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% polyacrylamide, and any range or amount therein). In other embodiments, the cushions comprise about 35% to about 45% polyacrylamide. In representative embodiments, the cushions comprise about 40% polyacrylamide. After centrifugation at room temperature, the pigmented cells are recovered in the pellet, whereas other cells remain near the top of the cushion.

In some aspects of this invention, the RPE cells can be seeded on a material surface at a high density of at least about 40,000 cells to about 200,000 cells per square centimeter of material surface, and any range therein. Thus, in some aspects, the RPE cells can be seeded at a density of at least about 40,000, 45,000, 50,000, 55,000, 60,000, 65,000, 70,000, 75,000, 80,000, 85,000, 90,000, 95,000, 100,000, 105,000, 110,000, 115,000, 120,000, 125,000, 130,000, 135,000, 140,000, 145,000, 150,000, 155,000, 160,000, 165,000, 170,000, 175,000, 180,000, 185,000, 190,000, 195,000, 200,000 cells per square centimeter of material surface. In particular embodiments, the RPE cells can be seeded at a density of at least about 50,000 cells to about 150,000 cells per square centimeter of material surface, and any amount or range therein. In representative embodiments, the RPE cells can be seeded at a density of at least about 40,000 cells per square centimeter of material surface. In further representative embodiments, the RPE cells can be seeded at a density of at least about 50,000 cells per square centimeter of material surface.

In particular embodiments, when porcine eyes are used, the cell populations isolated from two eyes can be used to establish a high density cell culture of about 20 $cm^2$ of cell culture surface.

The RPE primary cells can be grown in any general purpose cell culture media known in the art. The skilled artisan is able to determine the appropriate media from those known in the art and those later developed. Non-limiting examples of general purpose cell culture media include Eagle's minimal essential medium, Dulbecco's modified Eagle's medium (DMEM), Dulbecco/Vogt modified Eagle's minimal essential medium, Glasgow's Minimal Essential Medium, Glasgow's and/or Modified Eagle's Medium. In some embodiments, the general purpose culture media can further comprise fetal bovine serum. In some embodiments, the fetal bovine serum is present in the general purpose culture media at a concentration of about 1% to about 20%, about 5% to about 15%, or about 8% to about 12%, or any ranges therein (e.g., about 1%, 2%, 3%, 4%, 5%, 6%, 7%, 8%, 9%, 10%, 11%, 12%, 13%, 14%, 15%, 16%, 17%, 18%, 19%, 20%). In representative embodiments, the fetal bovine serum is present in the general purpose culture media at a concentration of about 10%. In other embodiments, the general purpose medium does not comprise fetal bovine serum.

In some embodiments, the cells in the RPE primary cell culture system are in a confluent monolayer on the material surface. In other embodiments, the subcellular deposits are formed in about 1 to about 14 days from the time the cells are seeded onto the material surface (e.g., about 1, 2, 3, 4, 5, 6, 7, 8, 9, 10, 11, 12, 13, 14 days from seeding).

In further embodiments, the present invention provides RPE primary cell culture systems producing subcellular deposits produced by the methods described herein.

As the first true model cell system exhibiting the pathogenic lesions (e.g., subcellular deposits such as drusen and BlinD) of macular degeneration, the RPE primary cell culture system of this invention can be used for studying the pathogenesis of macular degeneration and the abrogation of the lesions associated with this disease, and for evaluating therapeutic agents (e.g., agents, test agents, candidate agents, biological agents, chemical agents, therapeutic compositions, and the like) for the treatment and/or prevention of this disease. Thus, present invention also provides assays for determining the effect of candidate agents or candidate therapeutic compositions or treatments on the production of subcellular deposits by the RPE primary cell culture system of this invention. In one embodiment, the assay comprises contacting the agent, composition and/or treatment to the RPE primary cell system of this invention and determining whether the formation of the characteristic lesions (e.g., subcellular deposits) are reduced or prevented or whether further accumulation of said subcellular deposits is prevented.

Accordingly, in one aspect, a method of identifying a test agent that modulates the amount of subcellular deposits produced in an RPE primary cell culture system, comprising: contacting the RPE primary cell culture system of this invention with the test agent; and determining the amount of subcellular deposits produced by the RPE primary cell culture system contacted with said test agent as compared to a control RPE primary cell culture system not contacted with said test agent, wherein a test agent that increases or reduces the amount of subcellular deposits produced modulates the amount of subcellular deposits produced, thereby identifying a test agent that modulates the amount of subcellular deposits produced by the RPE primary cell culture system. Thus, in some aspects, a test agent that modulates the amount of subcellular deposits produced in an RPE primary cell culture system means that the test agent reduces the amount of subcellular deposits produced by said RPE primary cell culture system as compared to a control. In other aspects, a test agent that modulates the amount of subcellular deposits produced in an RPE primary cell culture system means that the test agent prevents the accumulation of subcellular deposits by said RPE primary cell culture system as compared to a control. In still other embodiments, a test agent that modulates the amount of subcellular deposits produced in an RPE primary cell culture system means that the test agent prevents further accumulation of the subcellular deposits produced by the RPE primary cell culture system as compared to the control. In representative embodiments, a control can be a RPE primary cell culture system of this invention that is not contacted with said test agent.

In other embodiments, a method for identifying an agent for treating macular degeneration is provided, comprising: contacting the RPE primary cell culture system of this invention with the agent; and determining the amount of subcellular deposits produced by the RPE primary cell culture system contacted with said agent as compared to a control RPE primary cell culture system not contacted with said agent, wherein an agent that reduces the amount of subcellular deposits produced by said RPE primary cell culture system contacted with said agent as compared to a control RPE primary cell culture system not contacted by said agent is identified as an agent for treating macular, degeneration.

In another embodiment, a method for identifying an agent for treating macular degeneration is provided, comprising: contacting the RPE primary cell culture system of this invention with the agent; and determining the amount of subcellular deposits produced by the RPE primary cell culture system contacted with said agent as compared to a control RPE primary cell culture system not contacted with said agent, wherein an agent that prevents the accumulation of subcellular deposits produced by said RPE primary cell culture system contacted with said agent as compared to a control RPE primary cell culture system not contacted by said agent is identified as an agent for treating macular degeneration.

In a further embodiment, a method for identifying an agent for treating macular degeneration is provided, comprising: contacting the RPE primary cell culture system of this invention with the agent; and determining the amount of subcellular deposits produced by the RPE primary cell culture system contacted with said agent as compared to a control RPE primary cell culture system not contacted with said agent, wherein an agent that prevents further accumulation of subcellular deposits produced by said RPE primary cell culture system contacted with said agent as compared to a control RPE primary cell culture system not contacted by said agent is identified as an agent for treating macular degeneration.

In further embodiments, methods for identifying an agent for preventing macular degeneration are provided, comprising: contacting the RPE primary cell culture system of this invention with the agent; and determining the amount of subcellular deposits produced by the RPE primary cell culture system contacted with said agent as compared to a control RPE primary cell culture system not contacted with said agent, wherein an agent that reduces the accumulation of subcellular deposits produced by said RPE primary cell culture system contacted with said agent as compared to a control RPE primary cell culture system not contacted by said agent is identified as an agent for preventing macular degeneration.

In still further embodiments, methods for identifying an agent for preventing macular degeneration are provided, comprising: contacting the RPE primary cell culture system of this invention with the agent; and determining the amount of subcellular deposits produced by the RPE primary cell culture system contacted with said agent as compared to a control RPE primary cell culture system not contacted with said agent, wherein an agent that prevents the accumulation of subcellular deposits produced by said RPE primary cell culture system contacted with said agent as compared to a control RPE primary cell culture system not contacted by said agent is identified as an agent for preventing macular degeneration.

In additional embodiments, the present invention provides methods for identifying an agent for preventing macular degeneration, comprising: contacting the RPE primary cell culture system of this invention with the agent; and determining the amount of subcellular deposits produced by the RPE primary cell culture system contacted with said agent as compared to a control RPE primary cell culture system not contacted with said agent, wherein an agent that prevents further accumulation of subcellular deposits produced by said RPE primary cell culture system contacted with said agent as compared to a control RPE primary cell culture system not contacted by said agent is identified as an agent for preventing macular degeneration.

As used herein, "contact," "contacting," (and grammatical variations thereof) the RPE primary cell culture system of this invention with an agent refers to placing the agent in the cell culture media comprising the RPE primary cell culture system for a period of time after which the cell cultures are assessed for the changes in the production of subcellular deposits as compared to a control RPE primary cell culture system that has not been contacted with the agent. The skilled artisan is able to determine the time period for contact of the RPE primary cell culture system with the agent, which can range from minutes to hours and/or days.

Various art-known assays are available for determining the amount of subcellular/extracellular lipid production by the RPE primary cell culture system. An exemplary assay for quantifying the amount of deposits present includes dark field photomicrography in which the white or light pixels can be counted using graphics programs including but not limited to ADOBE® PHOTOSHOP®. These and similar types of methods are well known in the art.

The present invention will now be described with reference to the following examples. It should be appreciated that these examples are for the purpose of illustrating aspects of the present invention, and do not limit the scope of the invention as defined by the claims.

EXAMPLES

Example 1

Establishment of a RPE Primary Cell Culture System

The methods used to procure animal tissues are approved by the Institutional Review Board at the University of Alabama at Birmingham. RPE cells are dissociated from porcine eyecups, purified and maintained in culture as previously described (citation IOVS 48:1892). Briefly, eyes enucleated from anesthetized animals are transported to the laboratory in sterile ice-cold normal saline. After removal of the anterior segment of the eye and the vitreous, the posterior eyecup is incubated in Leibovitz (L-15) medium; Invitrogen Corp., Carlsbad, Calif.) at room temperature for 30 minutes and the retina detached with forceps and scissors to expose the RPE monolayer. RPE cells are harvested by serial 30-minute incubations at 37° C. in 0.25% trypsin (Sigma-Aldrich, St. Louis, Mo.) in L-15 and collected by repeated gentle trituration with a 1-mL sterile pipette. To facilitate dissociation, trypsin-released RPE cells are incubated with 1% DNase enzyme (DNase I; Sigma-Aldrich) in L-15 for 2 minutes at room temperature.

Figure 3:
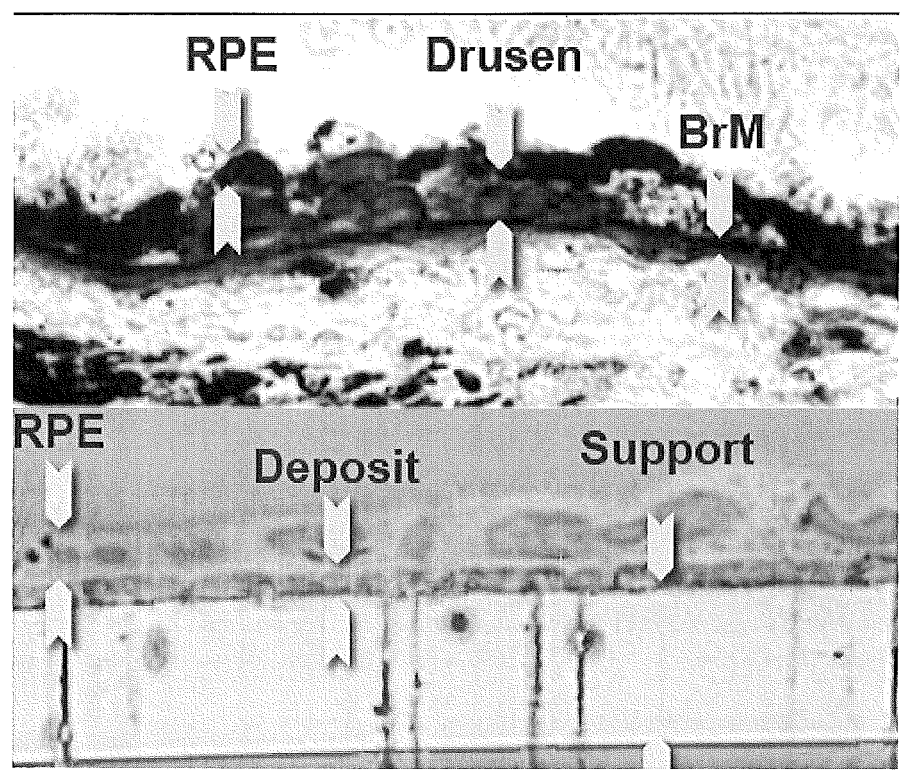
FIG. 3 shows (top) a human eye pathology specimen with AMD, stained for oil red O, a lysochromic dye used for neutral lipids (esterified cholesterol, triacylglycerol, free fatty acids, and vitamin A esters). Drusen exterior to the RPE and Bruch's membrane, exterior to the drusen, are stained intensely, indicating high concentration of neutral lipid.

The cells are further purified by density centrifugation on a cushion composed of a single-density gradient (Percoll 40%; GE Healthcare Biosciences Corp., Piscataway, N.J.) prepared with 0.01 M Na2PO4 and 0.15 M NaCl (pH 7.4). After centrifugation at 500 g for 3 minutes, the RPE cells were recovered as a pellet. Cells suspended in growth medium composed of Dulbecco's minimum essential medium (DMEM; Invitrogen) containing 20 mM 4-(2-hydroxyethyl)-1-piperazineethanesulfonic acid (HEPES; Mediatech, Inc., Herndon, Va.), 1% antibiotic-antimycotic (Invitrogen), and 10% fetal bovine serum (Invitrogen) were introduced into 100-mm tissue culture dishes (BD Biosciences, Franklin Lakes, N.J.) and incubated at 37° C. in a humidified atmosphere composed of 5% CO2 and 95% air. RPE isolates are routinely characterized by cytokeratin 18 content by our published immunochemical methods. (Mamballikalathil et al. *Invest. Opthalmol. Vis. Sci.* 41:529-536 (2000). See FIGS. 1A-1B, 2 and 3B, which show the RPE cell cultures and deposits. FIG. 3B shows that RPE has secreted lipoproteins into the basal chamber, filling the pores, and eventually creating the layer of deposits because egress through the pores is essentially blocked. The correspondence between the eye pathology specimen and the cell culture is striking.

Example 2

Assaying Agents for Modulation of the Production of Subcellular Deposits by the RPE Primary Cell Culture System A RPE primary cell culture system produced as described in Example 1 is contacted with a varying concentration of a candidate agent. The cell culture system is maintained in the presence of the candidate agent for varying periods of time and periodically assayed for changes in the production of subcellular deposits as compared to a control RPE primary cell culture system produced as described in Example 1 but not contacted with the candidate agent. The subcellular deposits produced by the RPE primary cell culture systems are quantified using, for example, dark field photomicrography. Changes that are observed in the RPE primary cell culture system that is contacted with the agent include decreased production of the subcellular deposits by; increased production of the subcellular deposits; prevention of the accumulation of the subcellular deposits; and/or prevention of the further accumulation of the subcellular deposits.

The foregoing is illustrative of the present invention, and is not to be construed as limiting thereof. The invention is defined by the following claims, with equivalents of the claims to be included therein.

That which is claimed is:

1. A retinal pigment epithelial (RPE) primary cell culture system, comprising:
    RPE primary cells seeded at a high density on a material surface and cultured without subculturing, wherein the RPE primary cells are harvested from non-fetal tissue; and
    a confluent layer of lipid-rich subcellular deposits between the RPE primary cells and the material surface.

2. The RPE primary cell culture system of claim 1, wherein the RPE cells of the cell culture system are contact inhibited and phenotype arrested.

3. The RPE primary cell culture system of claim 1, wherein the cells in the RPE primary cell culture system are in a confluent monolayer on the material surface.

4. The RPE primary cell culture system of claim 1, wherein the confluent layer of lipid-rich subcellular deposits comprises drusen and/or basal linear deposits.

5. The RPE primary cell culture system of claim 1, wherein the non-fetal tissue is from a mammal, a bird, a reptile, an amphibian, and/or a fish.

6. The RPE primary cell culture system of claim 5, wherein the mammal is a human, a non-human primate or a pig.

7. A method of identifying a test agent that modulates the amount of lipid-rich subcellular deposits produced in an RPE primary cell culture system, comprising:
    contacting the RPE primary cell culture system of claim 1 with a test agent; and
    determining the amount of lipid-rich subcellular deposits produced by the RPE primary cell culture system contacted with said test agent as compared to a control RPE primary cell culture system not contacted with said test agent, thereby identifying a test agent that modulates the amount of lipid-rich subcellular deposits produced by the RPE primary cell culture system.

8. The method of claim 7, wherein the test agent modulates the amount of lipid-rich subcellular deposits by reducing the amount of, preventing the accumulation of, or preventing further accumulation of the lipid-rich subcellular deposits produced by the RPE primary cell culture system contacted with the test agent as compared to a control RPE primary cell culture system not contacted with the test agent.

9. The method of claim 8, wherein the lipid-rich subcellular deposits comprise drusen and/or basal linear deposits (BlinD).

10. A method for identifying an agent for treating macular degeneration, comprising:
    contacting the RPE primary cell culture system of claim 1 with an agent; and
    determining the amount of lipid-rich subcellular deposits produced by the RPE primary cell culture system contacted with said agent as compared to a control RPE primary cell culture system not contacted with said agent,
    wherein an agent that reduces the amount of, prevents the accumulation of, or prevents further accumulation of lipid-rich subcellular deposits produced by said RPE primary cell culture system contacted with said agent as compared to a control RPE primary cell culture system not contacted with said agent is identified as an agent for treating macular degeneration.

11. A method for identifying an agent for preventing macular degeneration, comprising:
    contacting the RPE primary cell culture system of claim 1 with an agent; and
    determining the amount of lipid-rich subcellular deposits produced by the RPE primary cell culture system contacted with said agent as compared to a control RPE primary cell culture system not contacted with said agent,
    wherein an agent that reduces the amount of, prevents the accumulation of, or prevents further accumulation of lipid-rich subcellular deposits produced by said RPE primary cell culture system contacted with said agent as compared to a control RPE primary cell culture system not contacted with said agent is identified as an agent for preventing macular degeneration.

12. A method of producing a retinal pigment epithelial (RPE) primary cell culture system that produces a confluent layer of lipid-rich subcellular deposits, comprising:
    (a) seeding RPE primary cells on a material surface at a high density, wherein said RPE primary cells are harvested from non-fetal tissue; and
    (b) culturing the RPE primary cells seeded on said material surface without subculturing, thereby producing a RPE primary cell culture system that produces a confluent layer of lipid-rich subcellular deposits between the RPE primary cells and the material surface.

13. The method of claim 12, wherein the RPE cells are seeded at a density of 40,000 cells to about 200,000 cells per square centimeter of material surface.

14. The method of claim 12, wherein the confluent layer of lipid-rich subcellular deposits comprises drusen and/or basal linear deposits (BlinD).

15. The method of claim 12, wherein the RPE primary cells are subjected to high density centrifugation prior to seeding on the material surface.

16. The method of claim 12, wherein the RPE primary cells are from the eye of an organism excised from said organism 0 to 60 min post-mortem.

17. The method of claim 12, wherein the cells in the RPE primary cell culture system are in a confluent monolayer on the material surface.

18. The method of claim 12, wherein the non-fetal tissue is from an organism that is a mammal, a bird, a reptile, an amphibian, and/or a fish.

19. The method of claim 18, wherein the mammal is a human, a non-human primate or a pig.

20. A method of producing a confluent layer of lipid-rich subcellular deposits from a retinal pigment epithelial (RPE) primary cell culture system, comprising:
    (a) seeding RPE primary cells at a high density on a material support, wherein said RPE primary cells are harvested from non-fetal tissue; and
    (b) culturing the RPE primary cells seeded on said material support without subculturing, thereby producing a confluent layer of lipid-rich subcellular deposits between the RPE primary cells and the material support.

* * * * *